United States Patent [19]
Van Stokkum

[11] Patent Number: 6,080,135
[45] Date of Patent: Jun. 27, 2000

[54] AUTOMATICALLY ACTIVATED PROTECTION SYSTEM FOR HYPODERMIC NEEDLES

[76] Inventor: Petrus J. M. Van Stokkum, C/Vista Alegre, n°11, 07015 Palma De Mallorca, Spain

[21] Appl. No.: 09/361,070

[22] Filed: Jul. 26, 1999

[30] Foreign Application Priority Data

Aug. 26, 1998 [ES] Spain ................................ 9801613
Sep. 10, 1998 [ES] Spain ................................ 9801910

[51] Int. Cl.$^7$ .................................................. A61M 5/32
[52] U.S. Cl. ........................... 604/198; 604/192; 604/263
[58] Field of Search .................................. 604/198, 192, 604/195, 187, 263, 110, 164

[56] References Cited

U.S. PATENT DOCUMENTS

| | | | |
|---|---|---|---|
| 5,376,080 | 12/1994 | Petrussa | 604/198 |
| 5,411,487 | 5/1995 | Castagna | 604/198 |
| 5,549,558 | 8/1996 | Martin | 604/263 X |
| 5,554,131 | 9/1996 | Lacivita | 604/198 |

*Primary Examiner*—John B. Yasko
*Attorney, Agent, or Firm*—Michaelson & Wallace; Peter L. Michaelson

[57] ABSTRACT

A protection system applicable to hypodermic needles, which may be activated automatically, destined to cover the complete length of the needle once used in administering a drug, to prevent accidental jabbing, the system involving one or more individual protection components, concentrically arranged to each other and to the syringe nozzle when they are in a retracted position, capable of being successively dragged among each other when the release of the retention (or link-pin) means of the innermost one is produced, provoked by the action of a spring provided for such a purpose. Alternatively, the extendible component may adopt the shape of a bellows, enclosing in its interior the hypodermic needle of the syringe and dragging during its displacement a distal component like a tumbler, which incorporates at the inside face of its base a semi-ovoidal body consisting of sections which may be mutually brought together by elastic recovery and positioned against the needle to prevent return of the tumbler. The release of the mechanism is produced by the pushing action applied by link pins activated internally by means of a conical part.

8 Claims, 9 Drawing Sheets

AUTOMATICALLY ACTIVATED PROTECTION SYSTEM FOR HYPODERMIC NEEDLES

DESCRIPTION

The present invention refers to a new system intended to provide suitable protection to hypodermic needles used to inject drugs, thus preventing said needles from accidentally jabbing the specialist entrusted with their use and therefore, the possible contagion that may be derived from specific circumstances, particularly where diseases of the hepatitis or AIDS type are involved.

More specifically, the invention proposes the development of an absolutely novel protection system, activated automatically, that is, without having to be handled by the specialist or expert using the syringe, covering the whole length of the needle and once the combination of syringe stopper and piston has been displaced until the end of its run to inject the drug in the receiving patient, hence assuring that system activation is produced in any situation and therefore avoiding situation of forgetfulness by the user. The system is both simple and very versatile, since it may be coupled to any type of existing syringe, with important modifications, being possible to adapt it in different positions, both around the nozzle and in the extension thereof, partially surrounding the needle in the retracted position and being similarly applicable both in the case when the needle occupies a centred position with respect to the longitudinal axis of the nozzle, and when said needle is displaced with respect to said axis, as occurs in some cases of commonly used known syringes. In turn, the system permits the replacement of the needle whenever necessary.

BACKGROUND AND SUMMARY OF THE INVENTION

As is known, many situations exist in which medical personnel entrusted with the care of patients, are exposed to contagious environments derived from the fact that said personnel may accidentally jab themselves, due to the undue care or any other circumstance, with the needle of a syringe, once used to administer a specific drug to any patient under their care. This fact becomes especially relevant when said patients suffer from severe diseases, such as hepatitis C or AIDS.

With the purpose of preventing situations of the type mentioned above, the present invention has developed a system, whose activation is produced automatically and without need of any intervention or manipulation, providing protection of the needle just used to inject the drug.

The system of the invention is based on the use of some needle protection devices, which may be activated when the injection of the drug in question is being terminated, that is when the syringe stopper is about to reach the end of its run, when release devices of the protection devices are activated and which extend to cover the needle along its entire length and being designed such that once extended they cannot retract, hence assuring that the end of the needle is no longer uncovered and within reach of the user. The mentioned means of needle protection have been designed as from one or more individual components, suitably arranged around the syringe body or nozzle before being activated, concentrically with the latter and capable of being automatically extended, preferably by means of a spring, when the mentioned release is produced.

According to the invention, the system provides a set of possibilities, such as:

1) At its upper external end, where the injecting needle is adjusted, the nozzle incorporates around itself some cones and/or tumblers of a conical and/or cylindrical shape, which are interlocked and/or coupled, one inside the other forming a sort of cylindrical, conical or extended tube and depending on the measurement and quantity of cones and/or tumblers, the length of the cylindrical tube may be extended or shortened according to the size and length of the injecting needle.

2) The needle may be both fitted inside and/or outside the syringe.

3) The needle is fitted in the upper end of the nozzle, independently through the inside or outside, in turn around the needle and/or the part where it is coupled, there is a spring, which is fastened and/or fitted over a lengthened cylindrical surface which, in turn, may support the injecting needle.

When the needle is fitted inside the nozzle, the spring and its corresponding parts may be directly fitted over the needle.

4) The tumblers and/or cones are designed such that they perfectly fit inside each other, but at their ends, both upper and lower, they have a hook shape, such that on unfolding they are fastened inside each other, being it possible to pile an unspecified quantity of them to obtain any measurement and/or length.

5) The first tumbler and/or cone, located at the outside end and/or outside part of all of them, will be fitted to the nozzle to hide and fasten the rest of the tumblers, being it possible to dismantle and/or fix the combination over the syringe.

The combination of tumblers and/or cones may be manufactured separately, to fix them at a later date over any syringe, making small changes to said syringe but only in the extreme neck where the needle is usually adjusted and adding the trunco-conical protrusion to the piston so it may activate the mechanism.

6) The last tumbler, internally nearest to the injecting needle, will incorporate a support and/or washer with the purpose of fastening the spring and keeping it compressed. It will also include some parts to fasten to the syringe and hence overcome the pressure exerted over it by the spring, when in its initial position, before using the syringe.

Once the mechanism, has been activated automatically by the pushing motion applied manually over the stopper and piston, for the trunco-conical protrusion to activate the parts fastening the spring and, in turn, the tumbler and hence released, it is then that the spring will push the last tumbler upwards dragging the rest.

7) All the tumblers will be embedded in each other, one fitting in the other in the initial position. For this to occur, the first tumbler (outside) will be fixed to the nozzle and the rest inside and the last tumbler (nearest to the needle) will keep the spring around the upper neck and/or injecting needle compressed and in turn will remain fastened to the nozzle by some parts designed for such a purpose. To overcome the pressure exerted by the compressed spring, these parts will be in contact with other parts fitted in the upper inside part of the nozzle, being those which will finally release the first cone/tumbler permitting the spring to expand and pushing the tumbler and the rest of them upwards, permitting their function to be satisfied, namely that of protecting the needle from possible undesired jabs.

8) To prevent the mechanism from accidental activation before using the syringe, there are several safety devices.

According to the invention, an alternative method to carry out the preferred embodiment has been foreseen involving the use of a component configured like a bellows, which is fastened at its proximal end to the syringe nozzle, whilst at its distal end it incorporates a component like a tumbler provided with consistent retention devices, preferably, in short sections directed orthogonally towards the inside, related to flexible sections of the inside wall of the mentioned tumbler component and opposite at least a pair of mobile release parts, crossing the nozzle wall and susceptible to be pushed from inside by an extreme, conical section of a part interlocked to the stopper-piston combination and displaced with it. When said release occurs, the bellows is pushed forwards in the direction of the needle, due to the recovery of a spring which in the rest position is compressed, such that the length of the part in the bellows mode, which is greater than the hypodermic needle, permits the mentioned needle to recover in its total length. Moreover, the extreme tumbler part related to said bellows has a semi-ovoidal wall directed towards the inside space and divided in sections by means of appropriate cuts in a longitudinal direction. This wall is of elastic material, such as plastic or any other suitable one, such that when the bellows is stretched and the tumbler displaced forwards together with it, the elastic recovery of the mentioned wall material makes the different sections tend to approach each other, matching to form an extreme tip opposite the tip of the hypodermic needle itself, which evidently prevents the accidental or provoked return of the tumbler in the direction opposite to the extension in which it was displaced previously.

BRIEF DESCRIPTION OF THE DRAWINGS

Other features and advantages of the present invention will be shown by means of the following detailed description of a preferred embodiment referring to the attached drawings thereof, in which.

DESCRIPTION OF THE PREFERRED EMBODIMENTS

To make the detailed description of the preferred embodiments of the system of the invention, continuous reference will be made to the Figures of the drawings, through which the same references are used to identify equal or similar parts. Hence, firstly considering FIG. 1, a schematic view of a syringe section may be seen, which has been constructed according to the guidelines of the present invention. According to said representation, a syringe tube (1) of the conventional type appears which terminates at the end of a nozzle (2) at whose distal end an hypodermic needle (3) is adapted, also of the conventional type. In this representation, the hypodermic needle (3) appears axially centred with the syringe tube (1) and the nozzle (2), although as has already been said, the system to be described is likewise applicable to the cases in which the nozzle outlet and hence the hypodermic needle (3) are radially displaced outwards with respect to said longitudinal axis.

Figure 1:
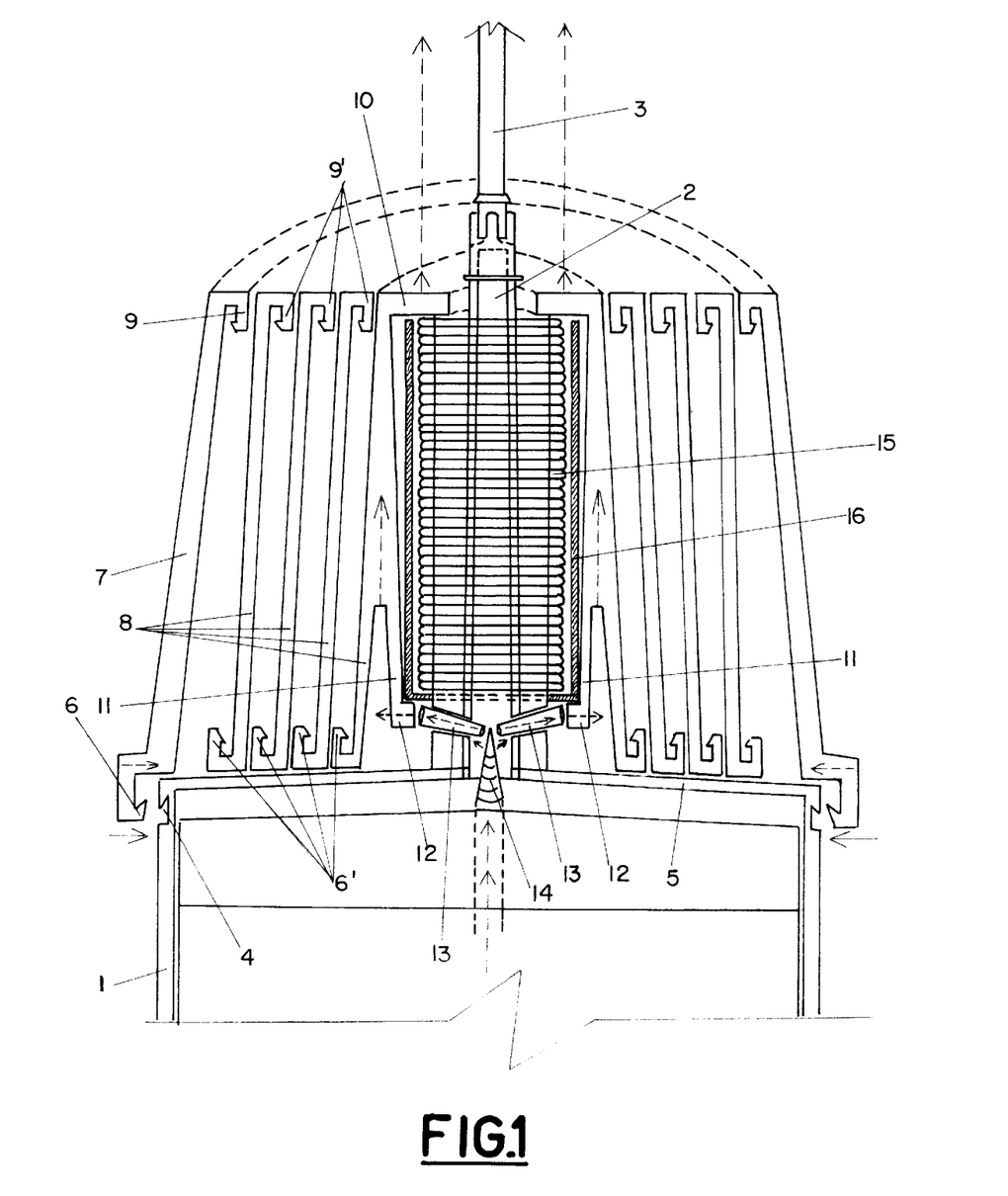
FIG. 1 is a schematic sectioned view of a syringe part and its corresponding nozzle, incorporating the system of the invention.

According to the invention, the syringe tube (1) incorporates a perimetric undercutting (4) next to its base, whose profile has been designed so as to be complemented with a part (6), like a hook, for which has been attached to an external part (7) or first tumbler of the combination foreseen for the system. As can be understand, the hooking between the tube (1) and the tumbler (7) section (6), may be any assuring a reliable retention, although a dove-tailing or similar system will be preferred. At the opposite end, the tumbler (7) has an annular tip, turned inwards and finished in a perimetric part forming a hook.

As can be seen in the Figure, the invention has foreseen that for the inside of the external tumbler (7), a variable number of other tumblers (8) are arranged, concentric with the one furthest from the center, formed in a similar way, namely with proximal hook sections (6'), consisting of annular hips turned outwards and finished in hooks and with distal hook sections (9') turned inwards and finished in the form of hooks. In all the cases, except for the innermost tumbler (8), that is, nearest to the nozzle (2), finished according to a wall (10) perpendicular to the longitudinal axis and provided with a wide central opening through which the tubular part of the nozzle (2) emerges, destined to be mutually coupled to the hypodermic needle (3).

Moreover, the innermost tumbler (8), has flexible side sections (11) integrated with the tumbler body, each one of which is finished at the proximal end by means of a section (12) directed inwards, each one of said sections (12) being opposite a respective part (13), like a latch and which may be displaced. Each latch part (13) is arranged by crossing the nozzle wall near to its joint with the tube (1) and with part of each latch introduced in the inside space of the nozzle orifice. On the other hand, it has been foreseen that the combination of syringe stopper and piston (not shown), includes an appropriate part (14) at its advance end, preferably conical, with suitable dimensions to be at least partially introduced inside the mentioned nozzle passage orifice.

Likewise, the system has foreseen the use of a spring (15) arranged around the nozzle, protected by a tubular component (16) surrounding it, closed at its proximal end and fastened to the nozzle (2) and open at the opposite end. The spring (15) leans at one end against the wall of said tubular protection component (16), whilst at the opposite end, it leans against the inside face of the innermost tumbler (8) wall (10).

In the position shown in FIG. 1, the combination is ready for use, with the spring (15) compressed and without the recovering force of said spring being able to displace the innermost tumbler (8), as the latter is retained in its position due to the support of the section (12) against the mentioned tubular component (16) surrounding the spring (15). On the other hand, and although the joint between the first tumbler (8) or outermost positioning and the syringe tube (8) appear in the hook position (6) separate from the housing (4), it will be understood that it is for purposes of illustration, as for the correct assembly of the system components, it is necessary that the hook (6) and the annular undercutting (4) are mutually coupled, with the existence of an effective union between them.

According to another characteristic of the embodiment shown in FIG. 1, the different tumblers (8) have such dimensions that they do not extend beyond the termination of the nozzle (2) area with the greatest diameter. This means, therefore, that the number of tumblers (8) should be such that together, they provide a length equal or slightly greater than the length of the nozzle and the hypodermic needle as a whole. Moreover, the shape adopted by the tumblers (8) will be that of cone-trunks with an extremely smooth conicity index, or completely cylindrical to be able to complete their function correctly.

As has been said above, the purpose of the system of the invention is to provide a protection means for the hypodermic needle after using and whose triggering is totally automatic, that is, without the use handling it in any way. This purpose has been completely satisfied with the embodiment described and consists of the following:

When a syringe of the type shown in FIG. 1 should be used, the user should handle it like any other, as the system incorporated in the nozzle (2) area, does not prevent the normal operation of the syringe. Moreover, the replacement of one needle by another may be made, whenever necessary, as there is no component impeding such an operation. When a drug is administered, the syringe stopper may make its run in the same way as any other syringe known, being it possible to use the hypodermic needle (3) in a conventional way. However, in comparison with known syringe models, when the drug has been injected and the stopper (not shown) is reaching the end of its run, the part (14) starts to introduce itself in the inside space of the longitudinal passage of the nozzle (2), until reaching the latch (13) positions, then and due to the latter's conicity, gradually pushes the latches (13) which are displaced outwards and in turn push the innermost tumbler (8) sections, which elastically give way until remaining beyond the component (16) limits retaining them, when, the pushing action made by the compressed spring (15) provokes the displacement of the innermost tumbler (8). When the latter has been sufficiently displaced, its corresponding hip (6') will hook into the hip (9') of the next tumbler and so on, whilst the spring exerts a pushing force and until the last tumbler (8) hooks onto its proximal hip (6') the distal hip (9) of the outermost tumbler (7). At this moment, no relative movement will exist between tumblers and in an outwards direction, that is around the needle, but as has been mentioned, the overall length provided by the tumblers will be sufficient to cover the total length of the needle.

Moreover, as will be easily understood, the shape adopted by the edges, namely hooks for each hip (6', 9, 9') mentioned, facilitates the hooking of each couple in front of each other when each tumbler reaches the end of its run. Moreover, this same shape prevents, once hooked together, that the tumblers be displaced in the opposite direction, hence maintaining the hypodermic needle totally hidden, and preventing possible accidental jabs by the person using it.

As will be understood, the system developed by the invention, in spite of being simple and easy to manufacture, provides absolute safety, once extended, against undesired jabs.

Figure 2:
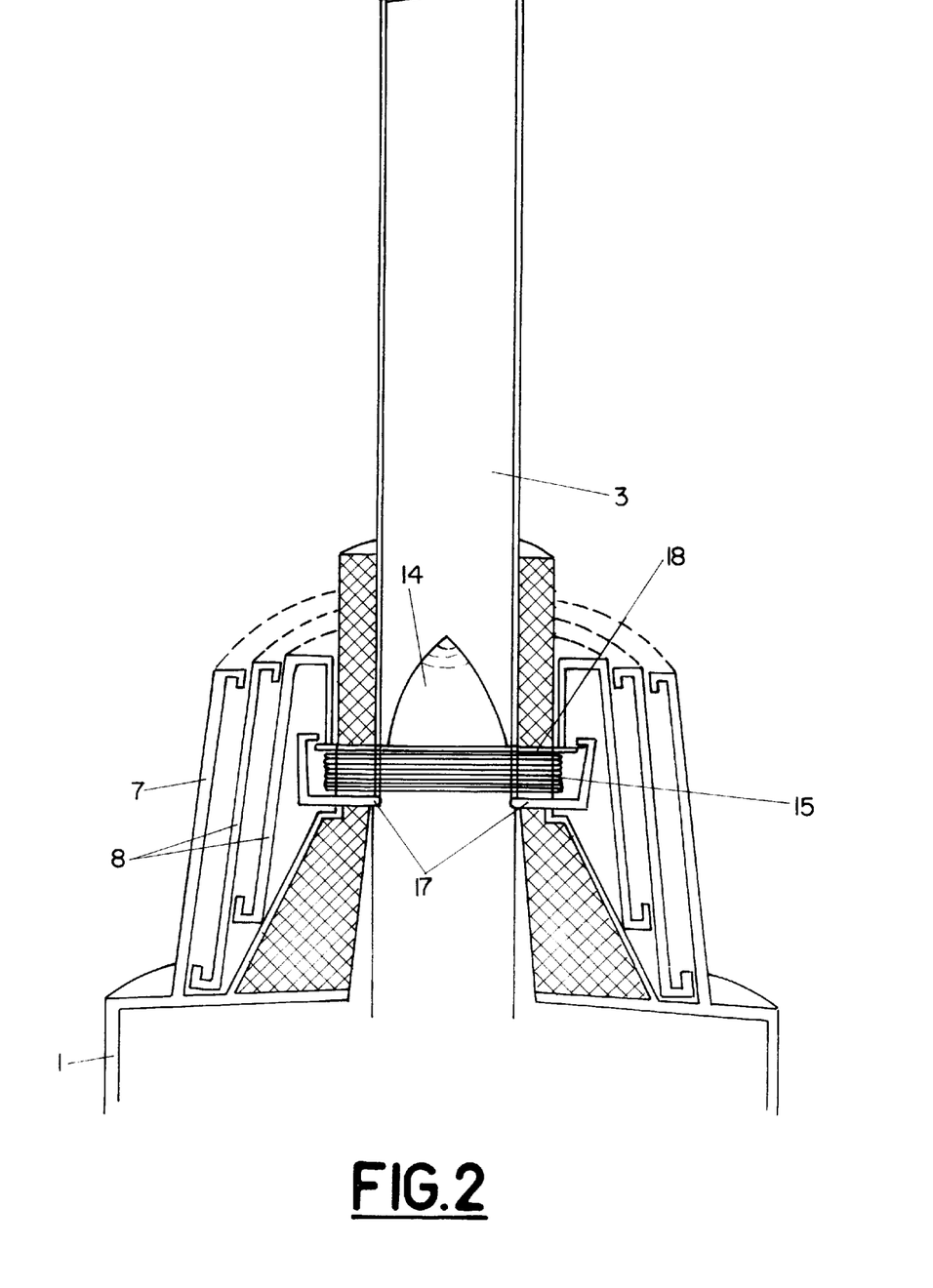
FIGS. 2 to 7 represent, respectively, different alternative embodiments of the system of the invention.

In FIG. 2, an embodiment of the invention is shown in which the outermost tumbler (7) is a continuation of the nozzle (2) itself and the remaining innermost tumblers (8) adopt concentric positions with the first, being finished with end hips for their respective mutual embedment, as has been described in reference to FIG. 1. In this case, the retention parts (17) act as the latches (13) of the previous Figure and are shaped such that their bodies presented by their distal ends folded inwards, fix the base (18) related to the innermost tumbler (8) in its position against the action of the spring (15). The push of the approximately triangular zone, determines the gradual outward push over said retention parts (17), such that with their displacement, the base (18) is released and hence that of the related tumbler (8) according to the recovery force of the spring (15) and therefore the successive dragging of all the tumblers until their extended position to cover the entire length of the needle (3).

Figure 3:
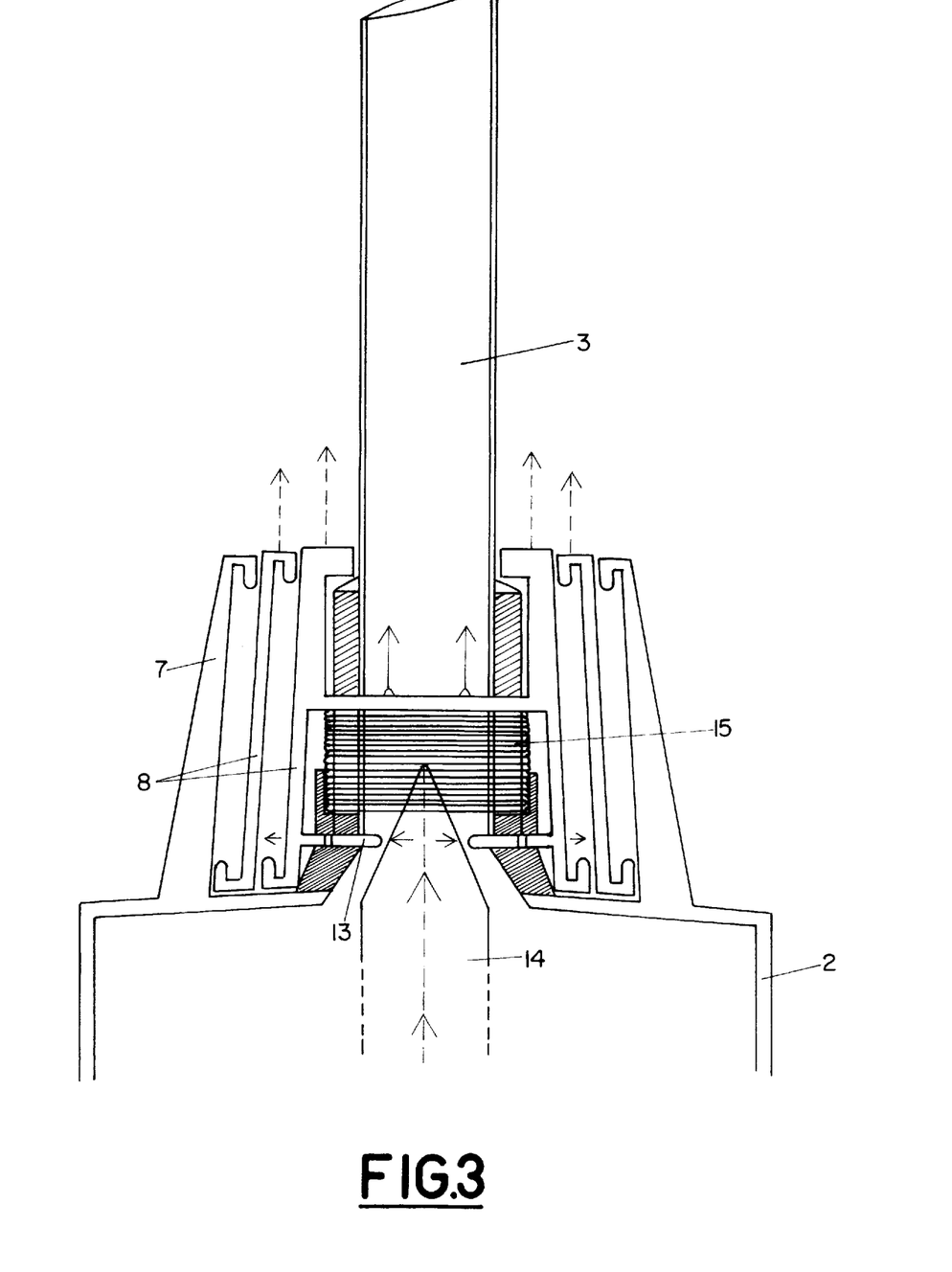

FIG. 3 shows an alternative embodiment, similar to that appearing in FIG. 2, likewise being provided with a first tumbler (7), the continuation of the nozzle (2), as well as the other inner tumblers (8), in a sufficient number, to cover the total length of the needle (3) in the position of the activated system, each tumbler having respective proximal and distal hips for the successive dragging in the way described and for which the innermost tumbler (8) has elastic proximal sections, in turn provided with sections introduced in the housing orifices of the latches (13), hence maintaining the innermost tumbler (8) retained, as well as the remaining ones and said latches (13) acting, when pushed through the area (14), over the sections of the elastic parts of the innermost tumbler (8) to provoke their release from the holes in which they are introduced and as a result, the release of said innermost tumbler (8) so that it may be displaced by the action of the springs (15) and so that during displacement it drags the remaining tumblers.

Figure 4:
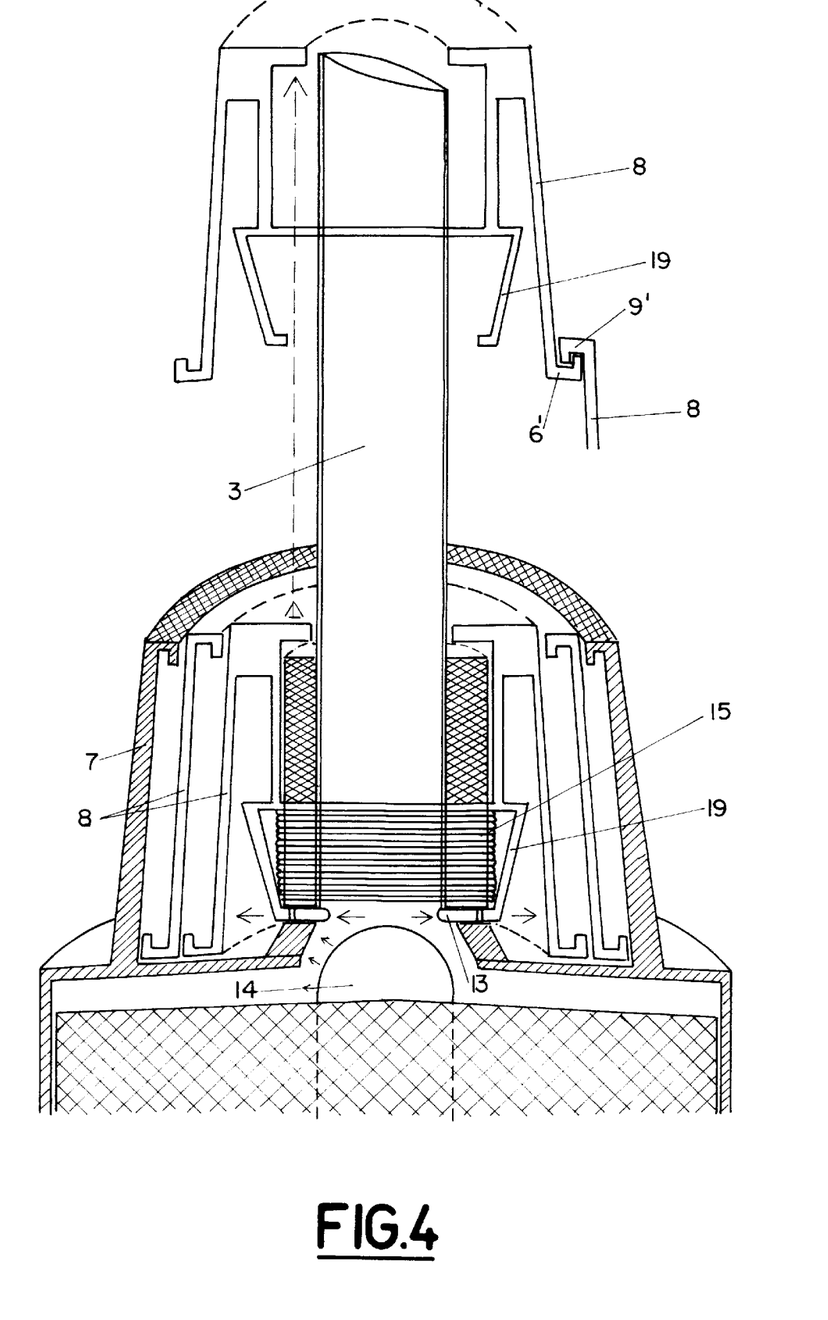

Referring to FIG. 4, an embodiment may be seen equivalent to that in FIG. 3, but with additional characteristics by which the innermost tumbler (8) has a double wall, where the innermost one has a proximal part (19) shaped like a cone trunk and which provides the upper hooking sections in the latch (13) housing orifices to be pushed by the latter due to the action over them by the zone (14) which in this case is shown as rounded. The spring (15) provides the pushing force for tumbler displacement. Moreover, in this same Figure, there is a schematic representation of the final position occupied by the innermost tumbler (8) once it has been displaced along its entire run, after release of its trunco-conical area (19), covering the tip of the hypodermic needle (3), and with the hips (6', 9') mutually coupled to each other.

Figure 5:
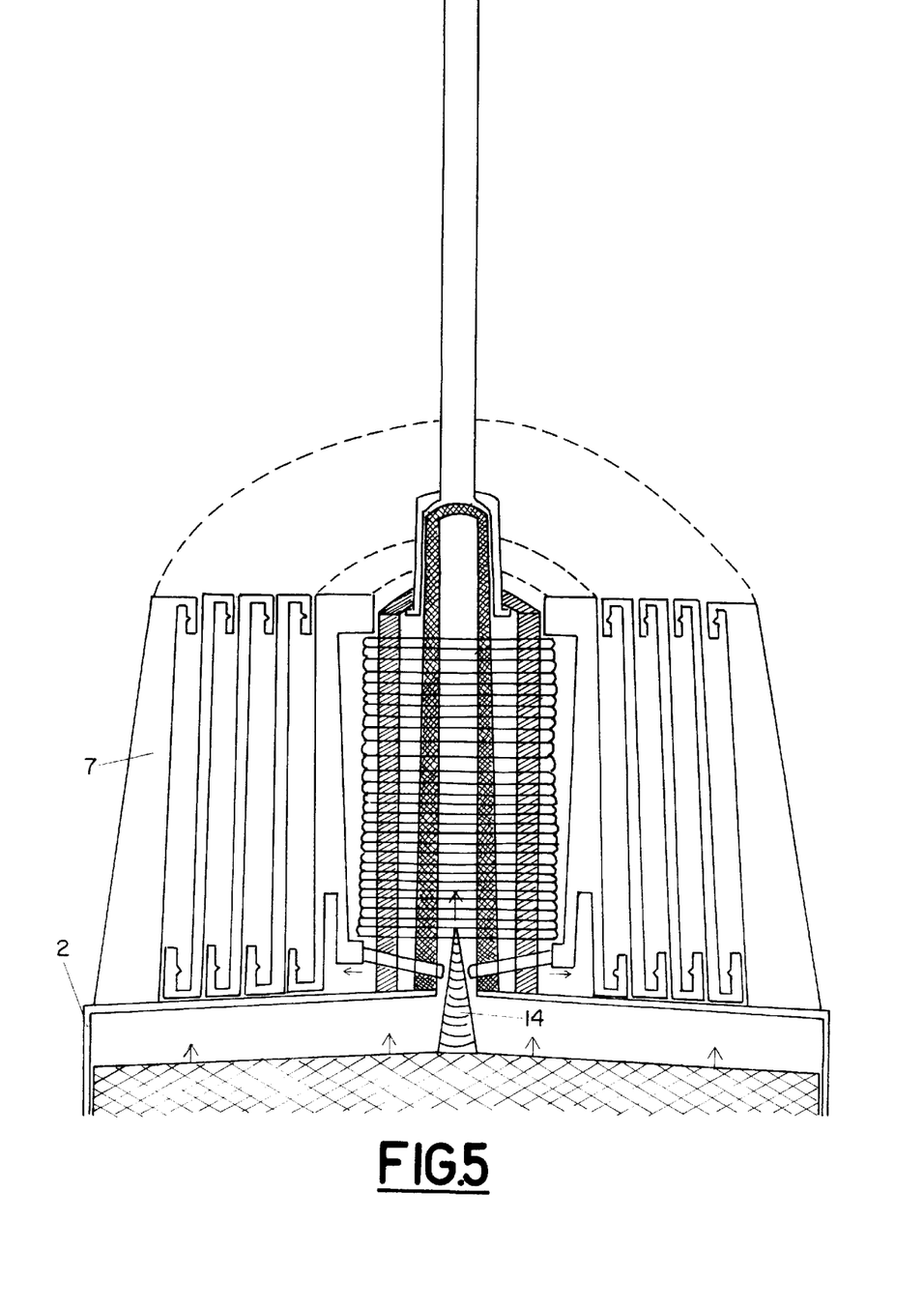

On the other hand, FIG. 5 shows an embodiment equal to that in FIG. 1, but with the variation that the outermost tumbler (7) appears as a continuation of the nozzle (2) itself. The operation is exactly equal to that already described FIG. 1.

Figure 6:
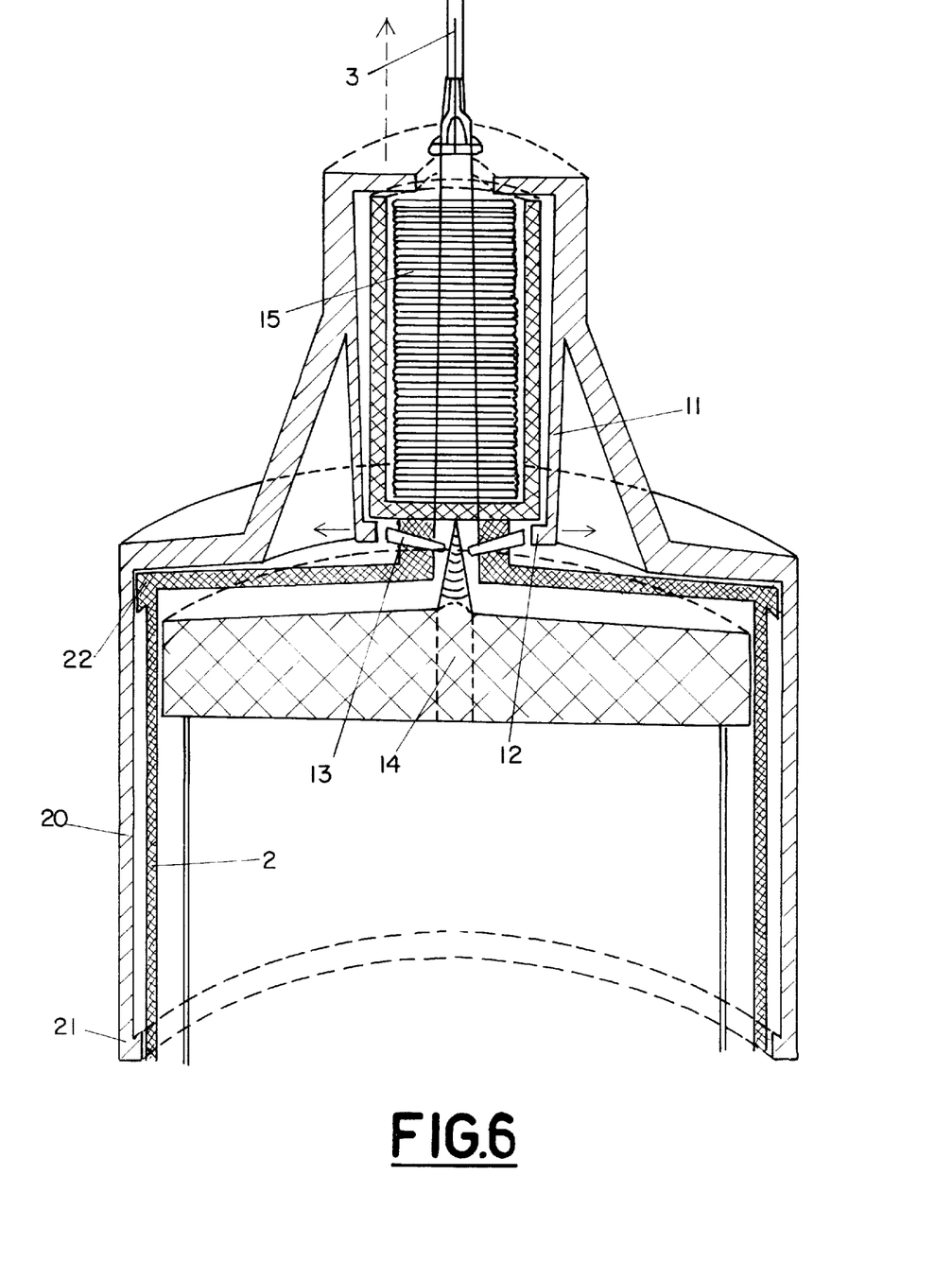
Figure 7:
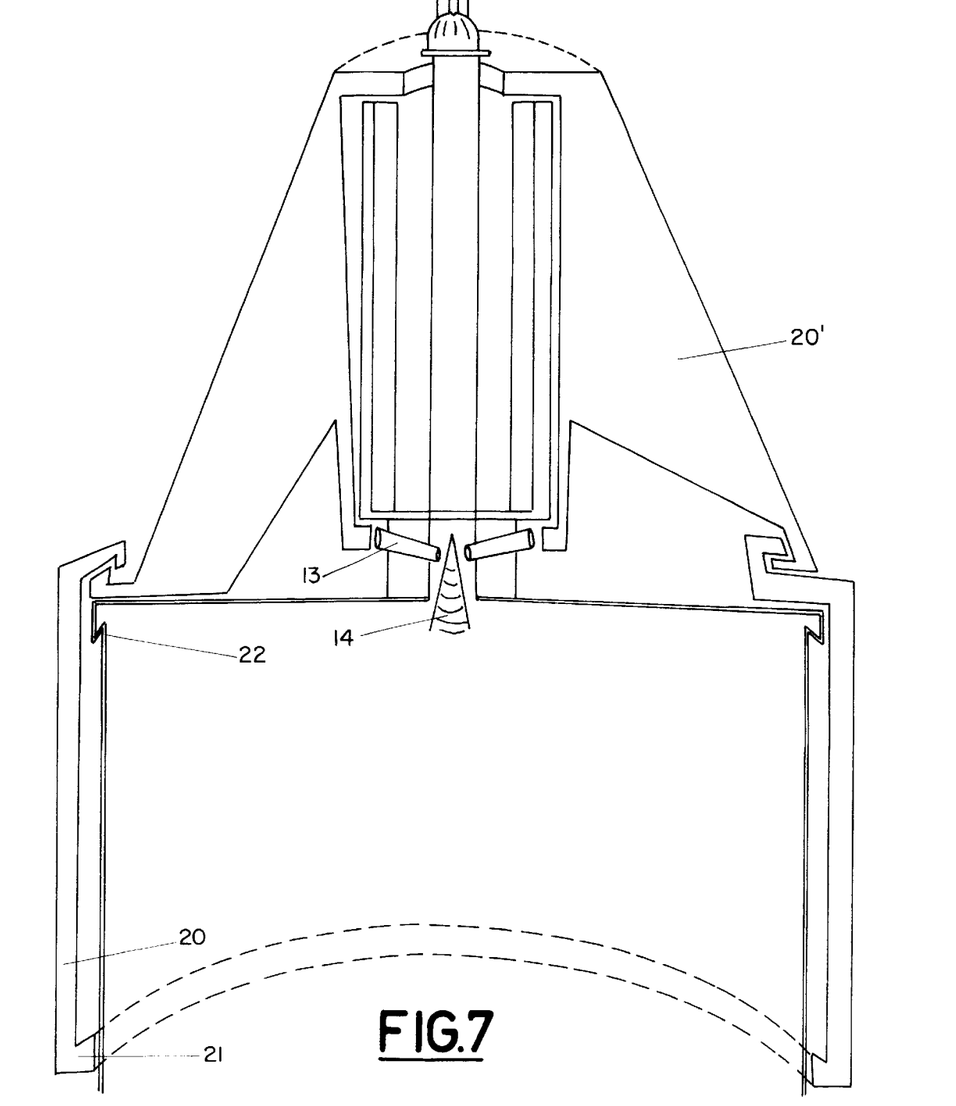

With respect to FIGS. 6 and 7, these show two examples of embodiments in which the number of tumblers necessary for the system to operate have been reduced. Firstly, observing FIG. 6, a single tumbler (20) may be seen, having a part extended with respect to the nozzle (2) and another extended to the distal outlet part thereof, in which the hypodermic needle (3) is coupled. This latter part has elastic protrusions (11) provided with short sections (12) by means of which it is kept retained to said tumbler against the action of the spring (15), said short sections (12) being opposite to latches (13) which may be activated by the part (14) related to the piston and stopper (not shown) of the syringe. In this case, the annular internal hip (21) of the tumbler (20) may be hooked in the complement (22) made next to the nozzle edge, when the pushing actions of the part (14) over the latches (13) provokes the release of the short sections (12) and hence the displacement of the single tumbler (20).

Nevertheless, in the case of the example of embodiment in FIG. 7, instead of being a single tumbler, an arrangement of two tumblers (20, 20') has been foreseen, respectively corresponding to the tumbler (20) parts differentiated in FIG. 6, such that retention and pushing effect is exerted over the tumbler (20') surrounding the nozzle, limits the run and displacement after release provoked by the part (14) and the latches (13) as already has been explained on repeated occasions. Hooking between the two tumblers (20, 20') is produced by means of respective adjacent hips, whilst limitation of the run is likewise executed when the tumbler (20) hip (21) reaches the hip (22) position provided to the nozzle at its extreme edge.

As will be understood, the described embodiments only corresponds to alternatives, being it necessary to interpret them as examples and it therefore being possible for any other combination to exist, either with each other or other components capable of giving a system equivalent to that described.

Figure 8:
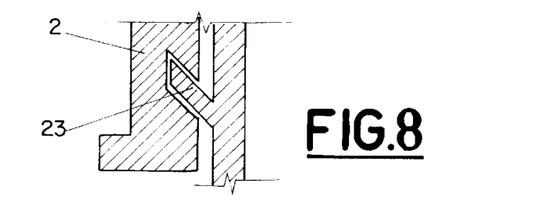
FIG. 8 illustrates a safety device foreseen for the invention to avoid accidental triggering of the system before its use.

FIG. 8 shows a device capable of assuring retention of the system against a possible accidental triggering provoking the possible extension of the system components, coverage of the hypodermic needle and hence the unserviceability of this syringe, due to the needle being hidden making its use impossible. For this purpose, it has been foreseen that the nozzle (2) has a slight groove to house a flange (23) fixed to the stopper and which prevents this from being displaced in the advance direction towards the needle. Now then, when a traction force is applied over the stopper, when about to use the syringe, said flange leaves its housing, moving towards the stopper and therefore permitting the stopper to perform its entire run in both directions. In this way, the desired protection against accidental triggering of the mechanism is provided.

Moreover, as will be easily understood, the system combines versatile characteristics making it suitable for use together with any type of syringe, it having been conceived for integrated manufacture with the former or to be incorporated later on.

Figure 9:
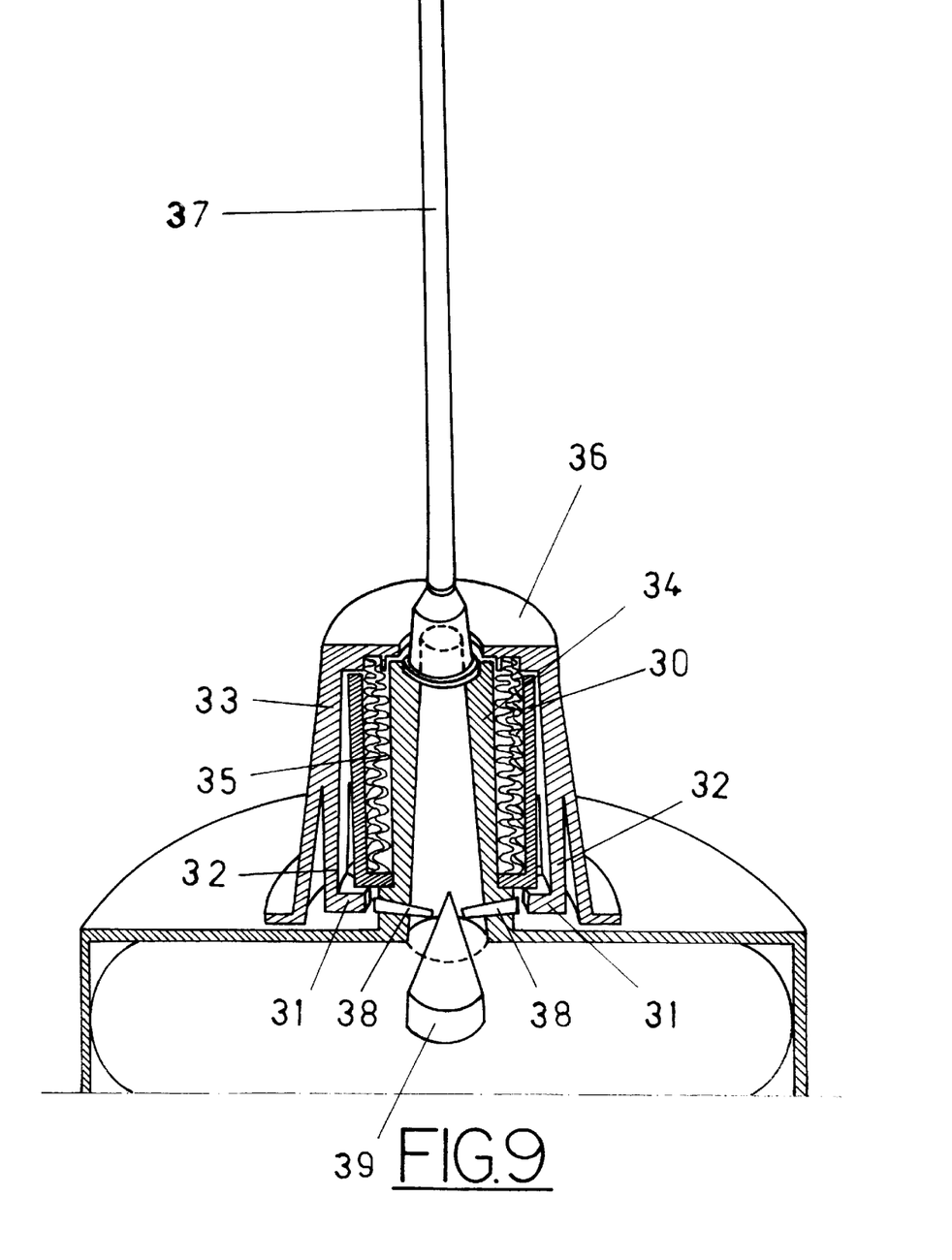
FIGS. 9 and 10 show a schematic perspective view of the components foreseen for the system of the invention for the execution of the optional second system in the respective positions of retraction and extension.
Figure 10:
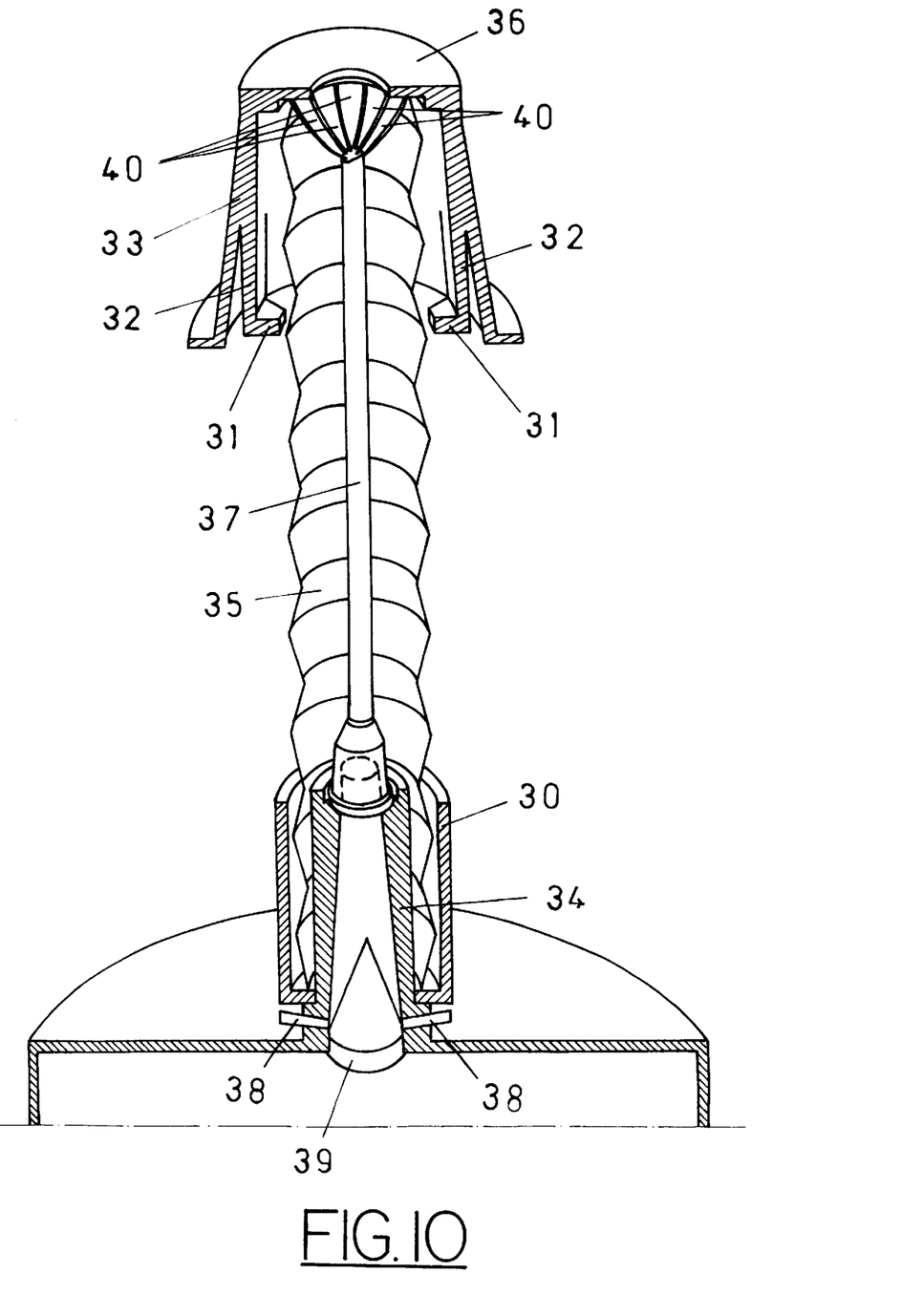

Observing now the FIGS. 9 and 10 of the attached drawings, a second optional preferred embodiment is shown, likewise providing the desired protection for the hypodermic needle used.

If we firstly examine FIG. 9, a perspective representation of the system of the invention is seen in the rest position, that is, gathered around the terminal part of the nozzle of an hypodermic syringe in which it is fitted. According to the representation of the Figure, the system includes a retention part (30), concentric with the mentioned terminal part of the syringe, of a predetermined length and having a seating on which two or more salients (31) are supported, directed orthogonally inwards, integral with respective sections (32), going towards the internal space from the corresponding face and an external part (33) preferably shaped like a trunco-conical tumbler (although this should not be considered as limiting, but only as the recommended shape for a preferred embodiment). As may be appreciated the retention part (31) is joined by its proximal part to that corresponding to the syringe nozzle, providing an internal space with respect to said terminal section (34) of the syringe nozzle, in which a component (35) is housed, capable of structuring, and may be activated by a spring preferably incorporated to the same. The mentioned bellows (35) leans, at its distal end, against the internal face of the base (36) provided with a tumbler part (33), said base having a central orifice through which the hypodermic needle (37) passes to the outside.

On the other hand, and which may also be observed in the mentioned FIG. 9, the invention incorporates one or more parts (38), preferably with inward directing salients (31), made as mobile components, or link pins, housed in transverse orifices made in the mentioned terminal part of the syringe nozzle, opposite the mentioned salients (31) and which may be pushed outwards when the conical section of a part (39) linked to the stopper-piston combination (not shown) of the syringe reaches in its longitudinal displacement, the position of the mentioned mobile components (38) motivated by the movement of said stopper-piston combination when a drug is administered with the syringe.

The pushing action applied over the mobile components (38) by the conical section of the part (39) during its longitudinal displacement, is transformed in a transverse displacement of said components (38), pushing the salient (31) outwards, such that when the displacement of said link-pins (38) is sufficient, said salients exceed the external perimetric position of the retention part (30), releasing the tumbler (33). In the totally extended bellows position, the hypodermic needle (37) remains totally closed inside the bellows and without possibility of later access. As can be understood, the release action of the mechanism which has already been mentioned corresponds to the moment when the combination of the syringe stopper and piston has been displaced enough, that is, when it reaches the end of its run and the conical section (39) introduces itself in the terminal part of the syringe.

In the released mechanism and extended bellows position commented previously, the system is as represented in FIG. 10. As may be seen, the wall (36) of the outside tumbler part (33), also incorporates at its external face a set of adjacent components (40), shaped in an approximate semi-ovoid body, thanks to several cuts made in a longitudinal direction in the mentioned body, preferably being integrated to said wall and constructed such that the sections or components composing it are capable of mutual approach once released, thanks to the elastic recovery of the material with which they are manufactured. These components have not been represented in FIG. 9 to simplify it, but obviously they are arranged around the terminal section (34) of the syringe. When release of the system is produced and the bellows displaces in a longitudinal direction to occupy the position of FIG. 10, these components (40) slide above the surface of the terminal section (34) of the syringe nozzle and above the surface of the hypodermic needle (37) itself. This method of execution provides the security that once the system has been released, no possibility exists, either accidental or purposely of making the tumbler (33) return, since the components (40) situated against the end of the hypodermic needle (37), prevent it. In this way, the disposal of the combination, once used, is assured, since it cannot be used again due to the needle being hidden and hence having lost its usefulness.

As will be understood, especially as from the representation of FIG. 9, the system is designed such that it permits the change of needle prior to administering the drug and hence prior to automatically triggering the bellows (35).

On the other hand, it will also be understood that the system is applicable to all kinds of needles, including existing ones, being possible to incorporate them to the syringe, both at the time of manufacture and at a later stage, as relevant.

On the other hand, the number of tumbler (33) components necessary for the correct operation of the system, may vary according to the requirements of each case. If several tumblers are used, these will occupy relative concentric positions and will have relative dragging devices.

Likewise, the system may incorporate devices for protection against the undesired, accidental triggering of the protection mechanism prior to drug administration. These devices, not represented for simplicity reasons, may consist of at least one flange linked to the stopper, which is housed in a groove made in the inside face of the syringe itself and which maintains the combination in its rest position until the user provokes the removal of the flange on applying traction on the mentioned stopper. Considering another embodiment of such devices for the prevention of an accidental activation, they may also consist of tabs linked to the external base or that of stopper pushing, such that before using the syringe, said tabs are introduced into an extension limited by a suitable stop and in such a way that when the syringe is going to be used, when introducing the drug in its inside, with the return movement of the stopper to suck the injectable material, said tabs abandon the inside space of the nozzle and may be folded outwards, manually or automatically, hence permitting the stopper to be displaced in any direction. As will be understood, while the mentioned tabs are arranged such that they prevent the advancing movement of the stopper, the part (39) cannot reach the position of the link-pins (38) and hence release of the mechanism cannot occur. It will also be understood that this method of retention against the undesired accidental release of the mechanism, represents only one of the possible solutions, being it possible to apply several other ones, without altering the operation of the release mechanism developed by the invention.

Also according to another alternative embodiments, if desired the tumbler (33) may simply consist of an extreme section linked to the base (36), from which elastic retention arms radiate in a longitudinal direction, hence considerably simplifying the manufacture of said part.

What is claimed is:

1. A protection system which, in conjunction with a hypodermic syringe, automatically provides protection to a hypodermic needle once the needle has been used with the syringe such that, once activated, the system covers a total length of the needle so as to prevent an accidental needle stick, wherein the system comprises:

link-pins crossing a nozzle body of the syringe;
   a spring situated along a longitudinal direction of the syringe and concentric with the nozzle body; and
   a protective component, displaceable along the longitudinal direction, comprising:
      at least one tumbler situated concentric with the nozzle body and the spring and abutting against an end of the spring, wherein at a rest position the one tumbler compresses the spring along the longitudinal direction, said one tumbler being shaped of a cylindrical or trunco-conical shape and provided with a dragging device, said device having:
         an annular hip; and
         at least one retaining component situated opposite the link-pins for retaining said one tumbler in its retracted position such that, when movement of a stopper in the syringe substantially reaches an end of its travel, a projection extending outward from the stopper acts upon the link pins so as to laterally move the retaining component and so release the one tumbler from its retracted position such that force exerted by the spring displaces the one tumbler along the longitudinal direction until action of the dragging device locks the tumbler in its extended position wherein, if a single tumbler is used, the one tumbler covers the total length of the needle and, if more than one tumbler is used, drags other remaining ones of the tumblers into their corresponding extended positions until all of the tumblers reach a position of maximum extension which covers the total length of the needle; and wherein the hip has a termination with a hook shape such that, if said one tumbler is used, once said one tumbler is extended, the hip prevents said one tumbler from being displaced in an opposite direction which would uncover the needle or, if multiple tumblers are used, once all the tumblers are extended all the terminations associated therewith prevent any of said tumblers from being displaced in the opposite direction which would uncover the needle.

2. The protective system recited in claim 1 further comprising a first retention device for preventing accidental activation of the system before use, the first retention device comprising a flange linked to the stopper and housed in a groove in an inside wall of the nozzle body and which keeps the system in the rest position until a user provokes removal of the flange when applying traction over the stopper.

3. The protective system recited in claim 1 further comprising:
   an extensible component of a bellows-like shape and of a pre-determined length having proximal and distal ends, the spring being housed in the extensible component and pressing against an external part, the external part having an internally cylindrical shape and linked to the distal end of the extensible component, wherein the external part comprises a first one of the tumblers and is concentrically positioned with the nozzle body; and
   a second one of the tumblers connected to the distal end of the extensible component and having an interior space with a wall extending around the interior space, the wall having a semi-ovoid shape and divided into a plurality of elastic sections resulting from cuts made in a longitudinal direction of the second one tumbler such that, due to elasticity of the first and second ones of the tumblers, the first and second ones of the tumblers engage with each other along their longitudinal central axis.

4. The protective system recited in claim 3 wherein the second one of the tumblers further comprises a plurality of second retention devices having a plurality of sections orthogonally directed inward and formed in respective elastic sections of inside walls of said second one of the tumblers, said retention devices situated opposite to and occupying, prior to activation of the system, mobile release components, wherein said the mobile release components cross a terminal section of the syringe nozzle and the second retention devices are capable of being pushed outwards to provoke the activation of the system when the mobile release components are pushed by the projection of the stopper.

5. The protective system recited in claim 3 further comprising a first retention device for preventing accidental activation of the system before use, the first retention device comprising a flange linked to the stopper and housed in a groove in an inside wall of the nozzle body and which keeps the system in the rest position until a user provokes removal of the flange when applying traction over the stopper.

6. The protective system recited in claim 2 further comprising:
   an extensible component of a bellows-like shape and of a pre-determined length having proximal and distal ends, the spring being housed in the extensible component and pressing against an external part, the external part having an internally cylindrical shape and linked to the distal end of the extensible component, wherein the external part comprises a first one of the tumblers and is concentrically positioned with the nozzle body; and a second one of the tumblers connected to the distal end of the extensible component and having an interior space with a wall extending around the interior space, the wall having a semi-ovoid shape and divided into a plurality of elastic sections resulting from cuts made in a longitudinal direction of the second one tumbler such that, due to elasticity of the first and second ones of the tumblers, the first and second ones of the tumblers engage with each other along their longitudinal central axis.

7. The protective system recited in claim 6 wherein the second one of the tumblers further comprises a plurality of second retention devices having a plurality of sections orthogonally directed inward and formed in respective elastic sections of inside walls of said second one of the tumblers, said retention devices situated opposite to and occupying, prior to activation of the system, mobile release components, wherein said the mobile release components cross a terminal section of the syringe nozzle and the second retention devices are capable of being pushed outwards to provoke the activation of the system when the mobile release components are pushed by the projection of the stopper.

8. The protective system recited in claim 6 further comprising a first retention device for preventing accidental activation of the system before use, the first retention device comprising a flange linked to the stopper and housed in a groove in an inside wall of the nozzle body and which keeps the system in the rest position until a user provokes removal of the flange when applying traction over the stopper.

* * * * *